United States Patent
Takahashi et al.

(10) Patent No.: US 11,291,354 B2
(45) Date of Patent: Apr. 5, 2022

(54) FLEXIBLE TUBE INSERTION APPARATUS AND FLEXIBLE TUBE INSERTION METHOD

(71) Applicant: OLYMPUS CORPORATION, Tokyo (JP)

(72) Inventors: Takeshi Takahashi, Hachioji (JP); Ryo Tezuka, Hachioji (JP); Shuji Nakamura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 316 days.

(21) Appl. No.: 16/445,859

(22) Filed: Jun. 19, 2019

(65) Prior Publication Data
US 2020/0000315 A1    Jan. 2, 2020

Related U.S. Application Data

(63) Continuation of application No. PCT/JP2016/088348, filed on Dec. 22, 2016.

(51) Int. Cl.
*A61B 1/00* (2006.01)
*A61B 1/005* (2006.01)
*A61B 1/31* (2006.01)

(52) U.S. Cl.
CPC .......... *A61B 1/0051* (2013.01); *A61B 1/0005* (2013.01); *A61B 1/00009* (2013.01);
(Continued)

(58) Field of Classification Search
CPC . A61B 1/0051; A61B 1/00009; A61B 1/0005; A61B 1/00071; A61B 1/00158;
(Continued)

(56) References Cited

U.S. PATENT DOCUMENTS

| 6,004,280 A * | 12/1999 | Buck ................. A61M 25/0041 600/434 |
| 2004/0044350 A1* | 3/2004 | Martin ................. A61B 1/0057 606/139 |

(Continued)

FOREIGN PATENT DOCUMENTS

| JP | 2003-093326 A | 4/2003 |
| JP | 2009-90023 A | 4/2009 |

(Continued)

OTHER PUBLICATIONS

English translation of International Preliminary Report on Patentability dated Jul. 4, 2019, together with the Written Opinion received in related International Application No. PCT/JP2016/088348.

(Continued)

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

A flexible tube insertion apparatus includes: a flexible tube to be inserted into an insertion target body; a state detector to detect state information of the flexible tube relating to a shape of the flexible tube; and a bent formation determining section to determine whether first and second bent portions bent in different directions are formed on the flexible tube based on the state information. The flexible tube insertion apparatus further includes a shape changing section, arranged in the flexible tube, to actively change the shape of the flexible tube so that an angle at which a first virtual flat plane on which the first bent portion is formed and a second virtual flat plane on which the second bent portion is formed intersect becomes smaller, when the bent formation deter- (Continued)

mining section determines that the first and second bent portions are formed on the flexible tube.

20 Claims, 11 Drawing Sheets

(52) U.S. Cl.
CPC ....... *A61B 1/00071* (2013.01); *A61B 1/00158* (2013.01); *A61B 1/31* (2013.01); *G06T 2207/30028* (2013.01)

(58) Field of Classification Search
CPC ....... A61B 1/31; A61B 1/0062; A61B 1/0065; A61B 5/062; A61B 5/7232; A61B 34/20; A61B 90/36; A61B 90/361; A61B 2034/2051; G06T 2207/30028
USPC .................................................. 600/101, 117
See application file for complete search history.

(56) References Cited

U.S. PATENT DOCUMENTS

| | | | |
|---|---|---|---|
| 2005/0228221 A1 | 10/2005 | Hirakawa | |
| 2009/0149703 A1* | 6/2009 | Tanaka | A61B 1/0051 600/103 |
| 2009/0221869 A1* | 9/2009 | Tanaka | A61B 5/416 600/103 |
| 2010/0191056 A1 | 7/2010 | Tanaka | |
| 2011/0098533 A1* | 4/2011 | Onoda | A61B 5/065 600/117 |
| 2011/0275896 A1* | 11/2011 | Tanaka | A61B 1/0016 600/118 |
| 2015/0342500 A1* | 12/2015 | Fujita | A61B 1/00131 600/117 |
| 2015/0351608 A1* | 12/2015 | Choi | A61B 1/00045 600/103 |

FOREIGN PATENT DOCUMENTS

| | | |
|---|---|---|
| JP | 4274854 B2 | 6/2009 |
| JP | 4789545 A | 10/2011 |
| JP | 2016-7434 A | 1/2016 |

OTHER PUBLICATIONS

International Search Report dated Mar. 14, 2017 issued in PCT/JP2016/088348.

* cited by examiner

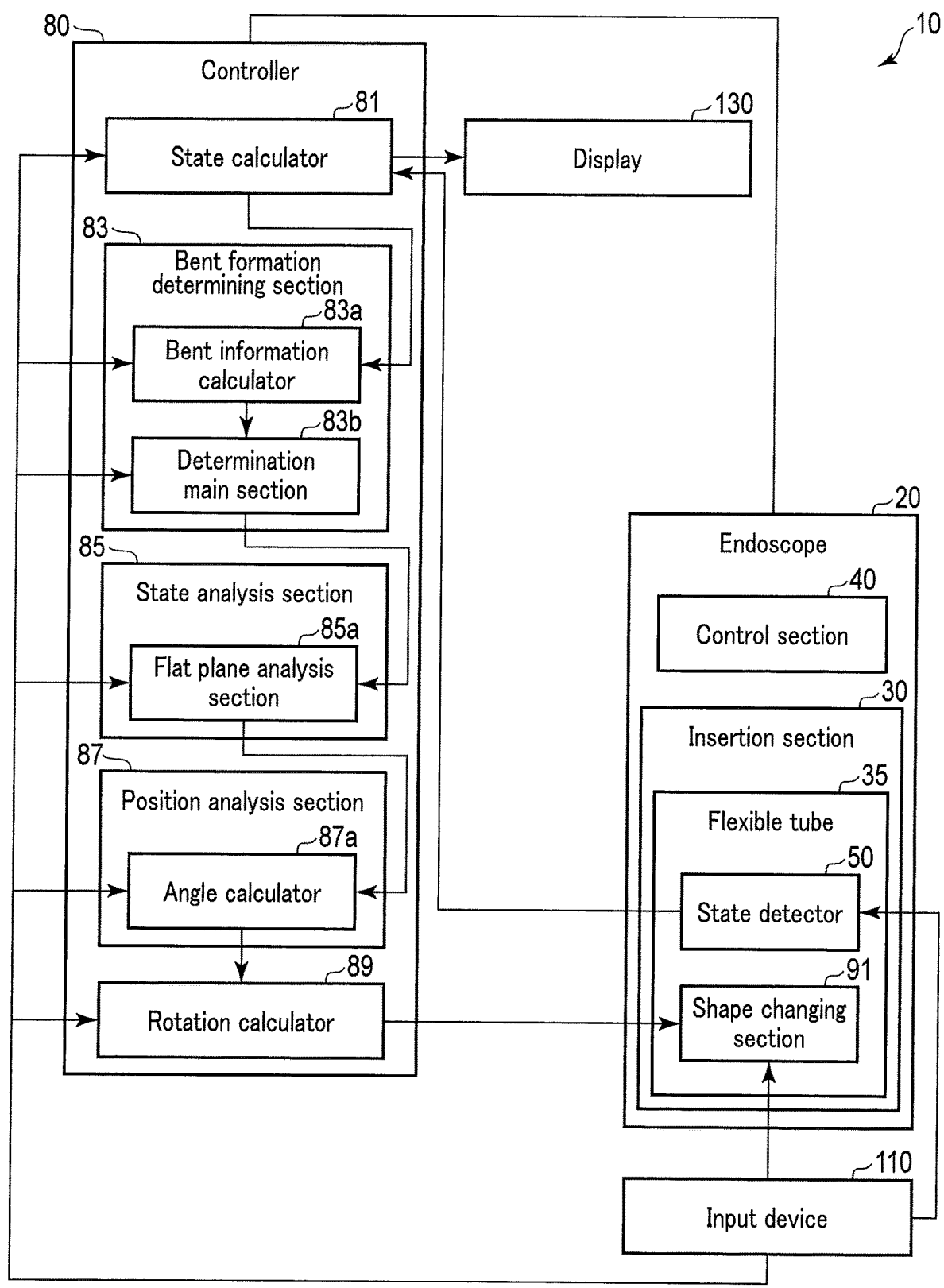
F I G. 1

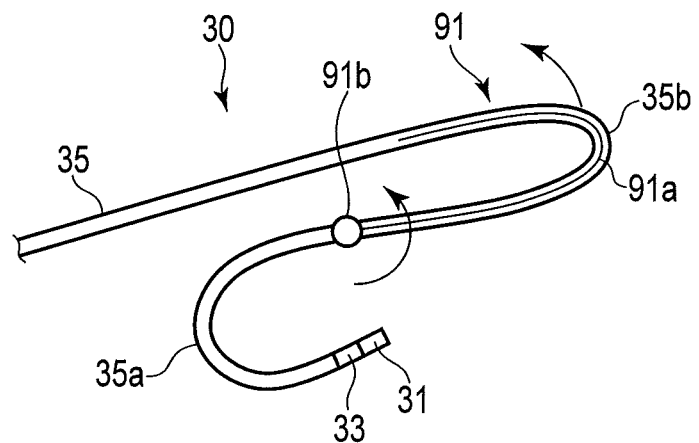
F I G. 5A
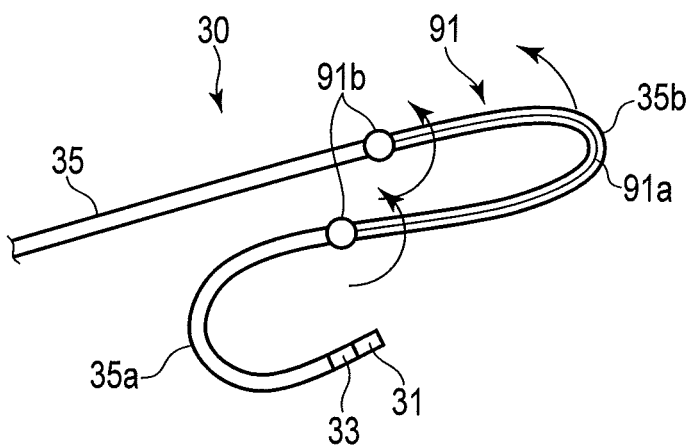
F I G. 5B

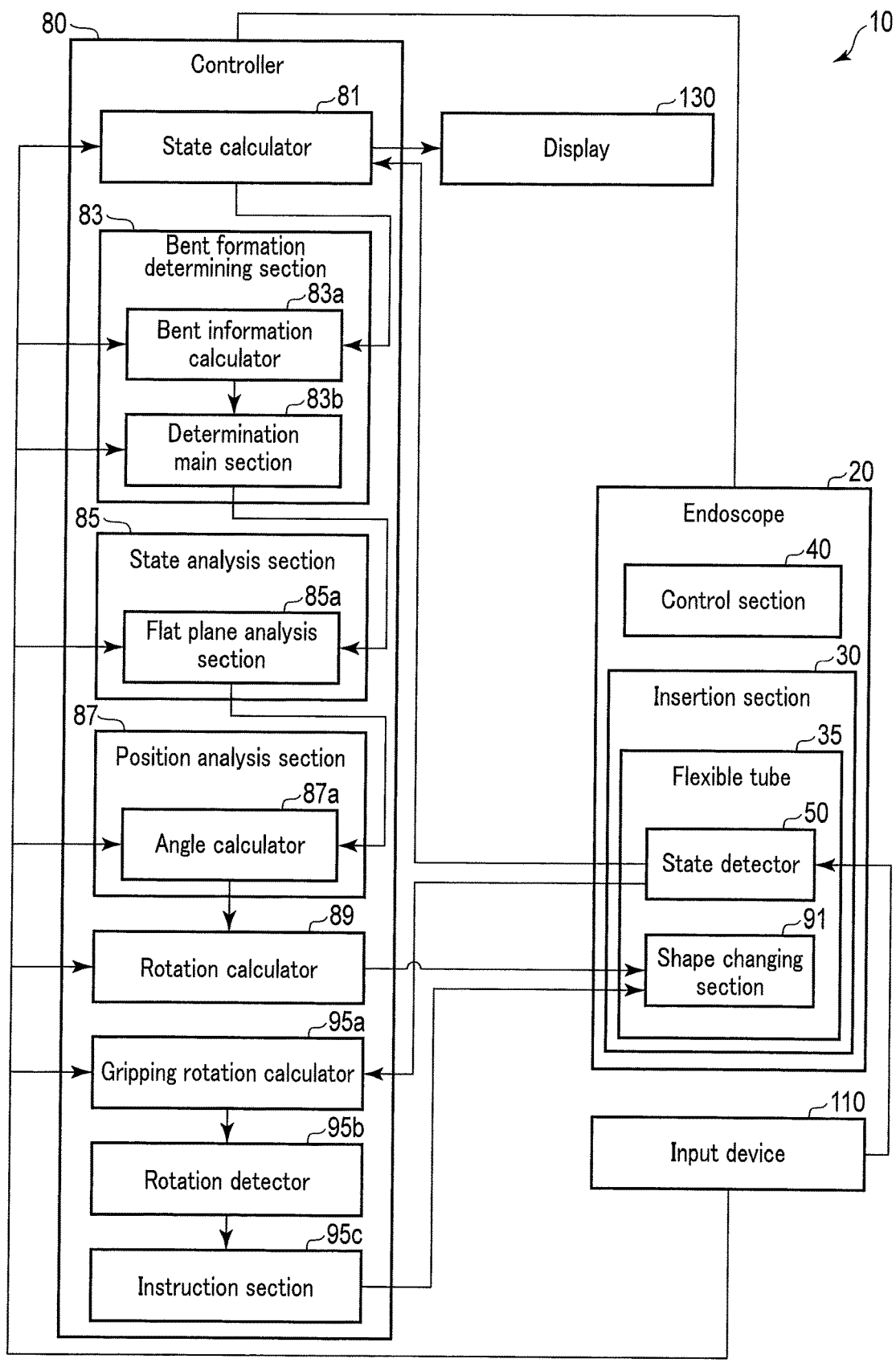
F I G. 6

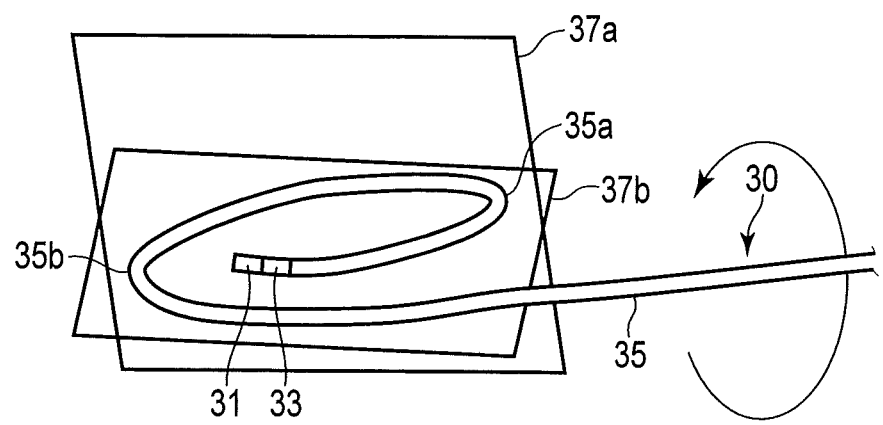
F I G. 8A
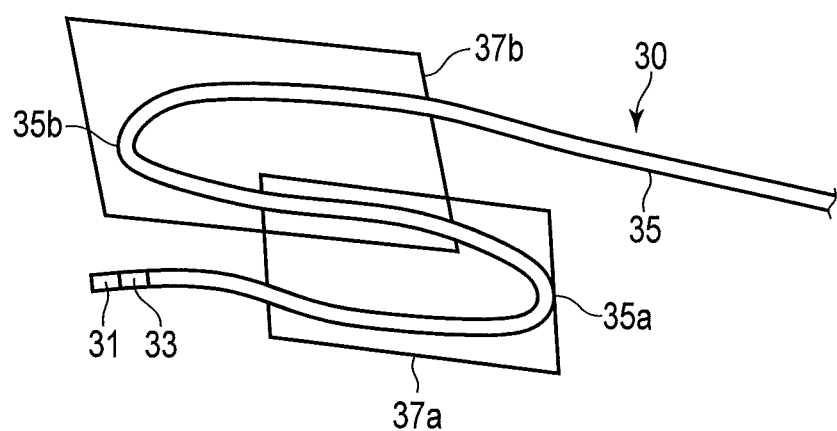
F I G. 8B

FLEXIBLE TUBE INSERTION APPARATUS AND FLEXIBLE TUBE INSERTION METHOD

CROSS-REFERENCE TO RELATED APPLICATIONS

This application is a Continuation Application of PCT Application No. PCT/JP2016/088348, filed Dec. 22, 2016, the entire contents of which are incorporated herein by reference.

BACKGROUND OF THE INVENTION

1. Field of the Invention

The present invention relates to a flexible tube insertion apparatus that is configured to insert a flexible tube toward a deep portion of a conduit portion of an insertion target body, and a flexible tube insertion method.

2. Description of the Related Art

For example, several insertion procedures have been known in which a distal end of a flexible tube of an endoscope is inserted (caused to proceed) toward a deep portion of an intestine tract of a large intestine. As an example of the insertion procedures, a substantially straightened procedure has been known. The substantially straightened procedure is described in the following.

It is assumed that the distal end of the flexible tube passes through a sigmoid colon to reach an SD bent portion. Herein, for convenience, a bent portion of the flexible tube at the SD bent portion is referred to as a first bent portion, and a bent portion of the flexible tube at the sigmoid colon is referred to as a second bent portion. A hand side of the flexible tube is subjected to, for example, rotation (twisting) operation of rotating (being twisted) about the longitudinal axis of the flexible tube by an operator who operates (grips) the hand side (proximal end side) of the flexible tube. The rotation force (twisting force) in the rotation operation is transmitted from the hand side to the second bent portion. Then, the entire second bent portion is rotated by the rotation force so that the entire second bent portion is lifted (raised) in the same direction as the rotation direction of the rotation force with respect the longitudinal axis on the hand side. That is, the direction of a flat plane on which the entire second bent portion is arranged is changed. At this time, the rotation operation is performed so that a second flat plane on which the entire second bent portion is arranged is arranged on a substantially identical flat plane with a first flat plane on which the entire first bent portion is arranged.

The rotation force is also transmitted to the first bent portion through the second bent portion. Then, the entire first bent portion pushes an intestine wall of the SD bent portion so that the distal end does not fall out from the SD bent portion. At this time, the flexible tube is subjected to drawing operation by an operator so that the distal end does not fall out from the SD bent portion. With the combination of the rotation operation and the drawing operation, the bending of the first and second bent portions is lost, and the flexible tube inside the large intestine is changed to substantially the straight shape. Further, by the rotation operation, the second flat plane is arranged on a substantially identical flat plane with the first flat plane. Thus, entanglement in the flexible tube is suppressed, and the flexible tube is changed to substantially the straight shape. The entanglement refers to twisting of the entire flexible tube, in other words, a state in which a loop portion is formed on the flexible tube as it is. Along with this change, the intestine tract from an inlet of the intestine tract to the SD bent portion at which the distal end of the flexible tube is arranged is changed to substantially the straight shape. Then, the pushing force on the hand side is easily transmitted to the distal end, so that the distal end of the flexible tube can easily proceed toward the deep portion by pushing.

Supporting information of such an insertion procedure is disclosed in, for example, Japanese Patent No. 4274854, Japanese Patent No. 4789545, and Jpn. Pat. Appln. KOKAI Publication No. 2016-7434.

BRIEF SUMMARY OF THE INVENTION

An aspect of the present invention is a flexible tube insertion apparatus. The flexible tube insertion apparatus includes: a flexible tube that is to be inserted into an insertion target body; a state detector that is configured to detect state information of the flexible tube relating to a shape of the flexible tube; and a bent formation determining section that is configured to determine whether or not a first bent portion and a second bent portion that are bent in directions different from each other are formed on the flexible tube based on the state information. The flexible tube insertion apparatus further includes a shape changing section that is arranged in the flexible tube and is configured to actively change the shape of the flexible tube so that an angle at which a first virtual flat plane on which the first bent portion is formed and a second virtual flat plane on which the second bent portion is formed intersect with each other becomes smaller, when the bent formation determining section determines that the first bent portion and the second bent portion are formed on the flexible tube.

Another aspect of the present invention is a flexible tube insertion method. The flexible tube insertion method includes: detecting state information of a flexible tube inserted into an insertion target body relating to a shape of the flexible tube; determining whether or not a first bent portion and a second bent portion that are bent in directions different from each other are formed on the flexible tube based on the state information; and causing a shape changing section that is arranged in the flexible tube and is configured to actively change the shape of the flexible tube to operate so that an angle at which a first virtual flat plane on which the first bent portion is formed and a second virtual flat plane on which the second bent portion is formed intersect with each other becomes smaller, when it is determined that the first bent portion and the second bent portion are formed on the flexible tube.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of a flexible tube insertion apparatus according to an embodiment of the present invention.

FIG. 5A is a diagram for illustrating an example of the shape changing section.

FIG. 5B is a diagram for illustrating an example of the shape changing section.

FIG. 6 is a diagram for explaining an example of operation start of the shape changing section.

FIG. 8A is a diagram for explaining rotation operation by the shape changing section in a state in which the first flat plane is arranged so as to be substantially orthogonal to the second flat plane.

FIG. 8B is a diagram for explaining the state in which the first flat plane is arranged on a substantially identical flat plane with the second flat plane by the rotation operation by the shape changing section.

DETAILED DESCRIPTION OF THE INVENTION

Figure 2A:
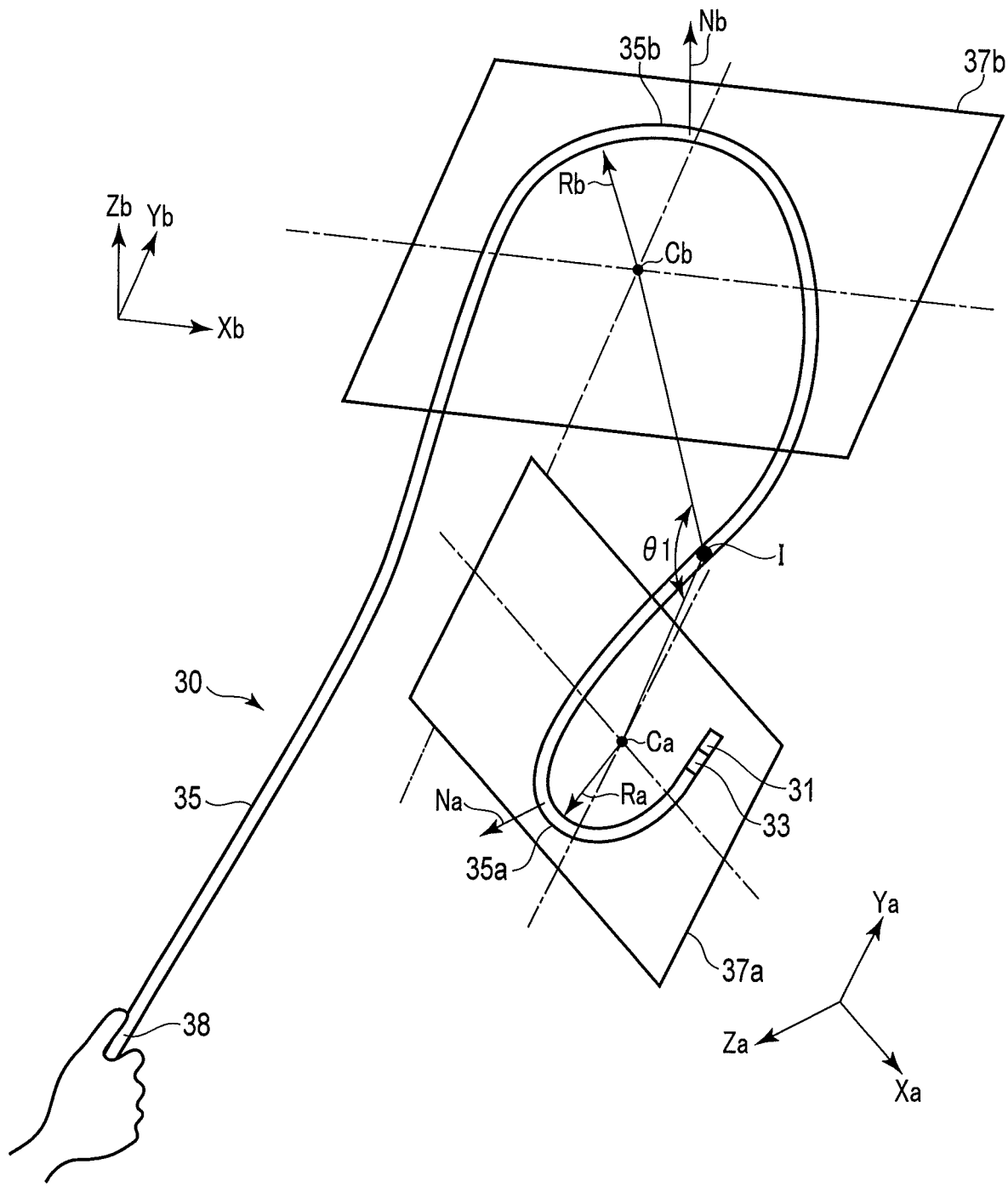
FIG. 2A is a diagram for explaining bent information of a flexible tube and respective shape states of bent portions.

Now, an embodiment of the present invention is described with reference to the drawings. Note that some members are omitted in some drawings for clarity of illustration.

As illustrated in FIG. 1, a flexible tube insertion apparatus (hereinafter referred to as an insertion apparatus 10) includes an endoscope 20, a controller 80 that is configured to control the endoscope 20, and an input device 110, and a display 130 connected to the controller 80. The controller 80 functions as, for example, a controller that is configured to perform control for assisting insertion of a flexible tube 35 of an insertion section 30 arranged in the endoscope 20. Although not illustrated, the insertion apparatus 10 may include a light source device that is configured to emit light used for observation and imaging by the endoscope 20.

The endoscope 20 is, for example, a flexible endoscope for medical use. The endoscope 20 may be, for example, a flexible endoscope for industrial use, a catheter, or a treatment instrument. It is only necessary that the endoscope 20 includes the flexible insertion section 30 to be inserted into a conduit portion (for example, an intestine tract of a large intestine) of an insertion target body (for example, a patient). It is only necessary that the insertion section 30 includes a portion having flexibility in which the insertion section 30 can be flexed by an external force applied from the outside of the insertion section 30 (for example, a flexible tube 35 described later). The external force refers to, for example, a reaction force or the like applied to the flexible tube 35 from an intestine tract wall around the flexible tube 35 or organs around the flexible tube 35 when the flexible tube 35 is inserted into the intestine tract. The endoscope 20 may be an endoscope 20 of a direct view type or an endoscope 20 of a side view type. An insertion target body is not limited to, for example, a human, and may be animals or other structures. The conduit portion may be, for example, a pipe for industrial use.

The endoscope 20 includes an insertion section 30, a control section 40 that is coupled to a proximal end of the insertion section 30 and is to be gripped by an operator of the insertion apparatus 10, and a universal cord (not shown) that extends from a side surface of the control section 40. The universal cord includes a connection portion (not shown) that is removably mountable to the controller 80.

The insertion section 30 is a tubular, elongated, and flexible. The insertion section 30 moves so as to advance and retreat relative to the conduit portion inside the conduit portion. The insertion section 30 includes an insertion body that is to be inserted into the conduit portion. As illustrated in FIG. 2A, the insertion section 30 includes a distal end hard section 31 and the flexible tube 35 in the order from a distal end from the insertion section 30 to the proximal end of the insertion section 30. The distal end hard section 31 is shorter than the flexible tube 35. Therefore, in this embodiment, the distal end hard section 31 and a distal end of the flexible tube 35 are regarded as the distal end of the insertion section 30. Further, the distal end of the flexible tube 35 includes a bendable section 33, the bendable section 33 is regarded as the distal end of the flexible tube 35, and the bendable section 33 is assumed to be included in the flexible tube 35. That is, the flexible tube 35 includes the bendable section 33 that is actively bent by operation by the control section 40, and a flexible section excluding the bendable section 33. The flexible section is bent passively by an external force. The flexible tube 35 has flexibility, and is flexed by an external force. The flexible tube 35 can be bent in conformity with the shape of the conduit portion. The bendable section 33 is bent in a desired direction by a knob (not shown) arranged in the control section 40.

As illustrated in FIG. 1, the insertion apparatus 10 includes a state detector 50 that is configured to detect state information of the flexible tube 35 relating to a state of the flexible tube 35 including the bendable section 33. The state information includes a bent state of the flexible tube 35 including the bendable section 33. The bent state of the flexible tube 35 includes, for example, a bending quantity of the flexible tube 35 including the bendable section 33 (magnitude of bending). The bending quantity is, in other words, a curvature radius or a curvature. The bent state of the flexible tube 35 includes a bending direction of the flexible tube 35 including the bendable section 33. The state information may include speed information. The speed information includes a magnitude of the speed and a direction of the speed of the flexible tube 35 including the bendable section 33 in a center axis direction of the flexible tube 35.

The state detector 50 includes, as an example, a fiber sensor utilizing a loss of a light transmission quantity due to bending of the optical fiber. The fiber sensor includes a light source (not shown) that is configured to emit light, an optical fiber (not shown) that is configured to guide light, and a reflector (not shown) that is configured to reflect the light guided by the optical fiber so as to be reversed through the optical fiber. The fiber sensor includes a light receiver (not shown) that is configured to receive the light reflected by the reflector, and a light branching unit (not shown). For example, the light source, the light receiver, and the light branching unit are mounted in the controller 80. For example, the optical fiber is incorporated in the endoscope 20, and the reflector is arranged in a distal end of the optical fiber arranged at the distal end of the insertion section 30. Although the state detector 50 is arranged in the endoscope 20 and the controller 80, for clarity of illustration, in FIG. 1, the state detector 50 is illustrated in the flexible tube 35 being one portion in which the optical fiber is arranged. The light source includes, for example, an LED or the like. The light source is separate from the light source of the light source device that is configured to emit light for observation and imaging. The optical fiber has flexibility. The optical fiber includes detection targets (not shown) mounted in the insertion section 30. The detection targets are arranged at positions different from each other in the longitudinal axis direction of the optical fiber. For example, the detection targets may be arranged at portions at which shape information of the flexible tube 35 is calculated described later, portions of being actively rotated described later (for example, a bent portion 35b described later), or the like. In this embodiment, the detection targets are arranged so as to be spaced apart at equal intervals from each other. The light receiver may include, for example, an element for spectral dispersion such as a spectroscope or a color filter, and a light receiving element such as a photodiode. The light source, the light receiver, and a proximal end of the optical fiber are optically connected to the light branching unit. The light branching unit includes, for example, an optical coupler or a half mirror. The light branching unit guides the light emitted from the light source to the optical fiber, and further, guides, to the light receiver, the return light reflected by the reflector and guided by the optical fiber. That is, the light proceeds in the order of the light source, the light branching unit, the optical fiber, the reflector, the optical fiber, the light branching unit, and the light receiver.

When the insertion section 30 is bent, the optical fiber is bent in accordance with this bending. In accordance with this, part of light propagating the optical fiber exits (leaks) to the outside through, for example, detection targets having sensitivities at different wavelengths. The detection targets change the optical characteristics of the optical fiber, for example, light transmission quantity of light having a predetermined wavelength. Therefore, when the optical fiber is bent, light transmission quantity of the light guided in the optical fiber is changed in accordance with the bending amount of the optical fiber. A light signal including information of change of the light transmission quantity is received by the light receiver. The light receiver outputs the light signal as the state information to a state calculator 81 described later arranged in the controller 80.

One detection target may be arranged in one optical fiber, and in this case, optical fibers are arranged. Further, it is assumed that the detection targets are arranged at the same position or positions close to each other in the longitudinal axis direction of the optical fiber and positions different from each other in a direction about the longitudinal axis direction. In this case, based on detection results of the detection targets, the bending amount and the bending direction can be detected.

The state detector 50 is not limited to including the fiber sensor. The state detector 50 may include, for example, any of a strain sensor, an acceleration sensor, a gyro sensor, and an element such as a coil. The strain sensor detects, for example, bending strain due to an external force (pressure) that is applied to the flexible tube 35 from the outside of the flexible tube 35 (for example, the inner circumferential wall portion of the conduit portion). The acceleration sensor detects acceleration of the flexible tube 35. The gyro sensor detects angular speed of the flexible tube 35. The element is, for example, a magnetic element that is configured to generate a magnetic field in accordance with the state of the flexible tube 35 such as the shape of the flexible tube 35.

The state detector 50 always performs detection (operates) after a detection start instruction is input from the input device 110 to the state detector 50. The timing of detection is not particularly limited, and detection may be performed for each elapse of a predetermined time. The state detector 50 is, for example, connected to the state calculator 81 by wire or wireless, and detection results detected by the state detector 50 are output to the state calculator 81.

The input device 110 is general equipment for input, and is, for example, a keyboard, a pointing device such as a mouse, a tag reader, a button switch, a slider, a dial, or a foot switch. The input device 110 may be used by an operator to input various instructions in order to operate the insertion apparatus 10. The input device 110 as a button switch may be incorporated in the control section 40 of the endoscope 20.

The display 130 displays an image imaged by an imaging unit (not shown). The display 130 includes, for example, a monitor. The imaging unit is incorporated in the insertion section 30, and includes, for example, a CCD and the like.

As illustrated in FIG. 1, the insertion apparatus 10 includes the state calculator 81, a bent formation determining section (hereinafter referred to as a determining section 83), a state analysis section 85, a position analysis section 87, a rotation calculator 89, and a shape changing section 91. The state calculator 81, the determining section 83, the state analysis section 85, the position analysis section 87, and the rotation calculator 89 are arranged in the controller 80. The arrangement position of the shape changing section 91 is described later. The state calculator 81 may be arranged as a separate device from the controller 80.

The state calculator 81, the determining section 83, the state analysis section 85, the position analysis section 87, and the rotation calculator 89 are configured by, for example, a hardware circuit including an ASIC or the like. At least one of the state calculator 81, the determining section 83, the state analysis section 85, the position analysis section 87, and the rotation calculator 89 may be configured by a processor. When at least one of those is configured by a processor, an internal memory or an external memory (not shown) to which the processor is accessible is arranged. The internal memory or the external memory stores a program code for causing the processor to function as at least one of those when the processor performs execution.

The state calculator 81 calculates, based on the state information detected by the state detector 50, shape information of the flexible tube 35 including the bendable section 33 relating to the shape of the flexible tube 35 including the bendable section 33 along the center axis direction of the flexible tube 35. For example, the state calculator 81 calculates shape information at a predetermined time based on the relationship of characteristics of incoming light to the optical fiber and outgoing light from the optical fiber. In detail, the state calculator 81 calculates shape information based on the state information output from the fiber sensor. Specifically, the state calculator 81 calculates the bent shape of the portion that is actually bent. The bent shape includes, for example, the bending amount and the bending direction of the portion that is actually bent.

The state calculator 81 outputs the shape information calculated by the state calculator 81 to the determining section 83. The state calculator 81 may output the shape information calculated by the state calculator 81 to the display 130, and the display 130 may display shape information. The state calculator 81 always performs calculation (operates) after a calculation start instruction output from the input device 110 is input to the state calculator 81 in the state in which detection results of the state detector 50 are input. The timing of calculation is not particularly limited, and calculation may be performed for each elapse of a predetermined time.

The determining section 83 calculates bent information of the flexible tube 35 including the bendable section 33 based on the shape information calculated by the state calculator 81. The determining section 83 determines whether or not two or more bent portions that are bent in directions different from each other (for example, see bent portions 35a and 35b illustrated in FIG. 2A) are formed in the flexible tube 35 based on the bent information. In other words, the determining section 83 determines whether or not the bent portion 35a and the bent portion 35b that is bent in a direction different from that of the bent portion 35a are present in the flexible tube 35 including the bendable section 33. For example, the bent portion 35b is bent in a direction opposite to that of the bent portion 35a. The determining section 83 includes a bent information calculator 83a and a determination main section 83b.

The bent information calculator 83a calculates bent information. The bent information includes, for example, the two bent portions 35a and 35b (see FIG. 2A) that are continuous from each other in the bendable section 33 in the flexible tube 35 including the bendable section 33, an inflection point I (see FIG. 2A), curvature radii Ra and Rb (see FIG. 2A) of the bent portions 35a and 35b, curvature centers Ca and Cb (see FIG. 2A) of the bent portions 35a and 35b, and an angle θ1 (see FIG. 2A). Description is made assuming that the bent portion 35a is located on the front side with respect to the bent portion 35b in an insertion direction of the flexible tube 35. Therefore, the bent portion 35a is a first bent portion arranged on the distal end side of the flexible tube 35, and the bent portion 35b is a second bent portion arranged on the proximal end side of the flexible tube 35. The bent portions 35a and 35b that are continuous from each other each represent an S-shaped portion (see FIG. 2A) of the flexible tube 35. The inflection point I is the continuous portion between the bent portion 35a and the bent portion 35b, and a point at which the curvature radius of the bent portion between the bent portion 35a and the bent portion 35b is ∞. The bent portions 35a and 35b are arranged with the inflection point I therebetween. The angle θ1 is an angle formed by line segments connecting the curvature center Ca, the inflection point I, and the curvature center Cb in the stated order.

In this embodiment, as an example, the inflection point I, the curvature radii Ra and Rb, and the curvature centers Ca and Cb regarding the bent portions 35a and 35b are described. However, in accordance with the number of bent portions, the number of inflection points involved by the bent portions and the curvature radius and the curvature center of each of the bent portions may be calculated as appropriate by the bent information calculator 83a.

Figure 2B:
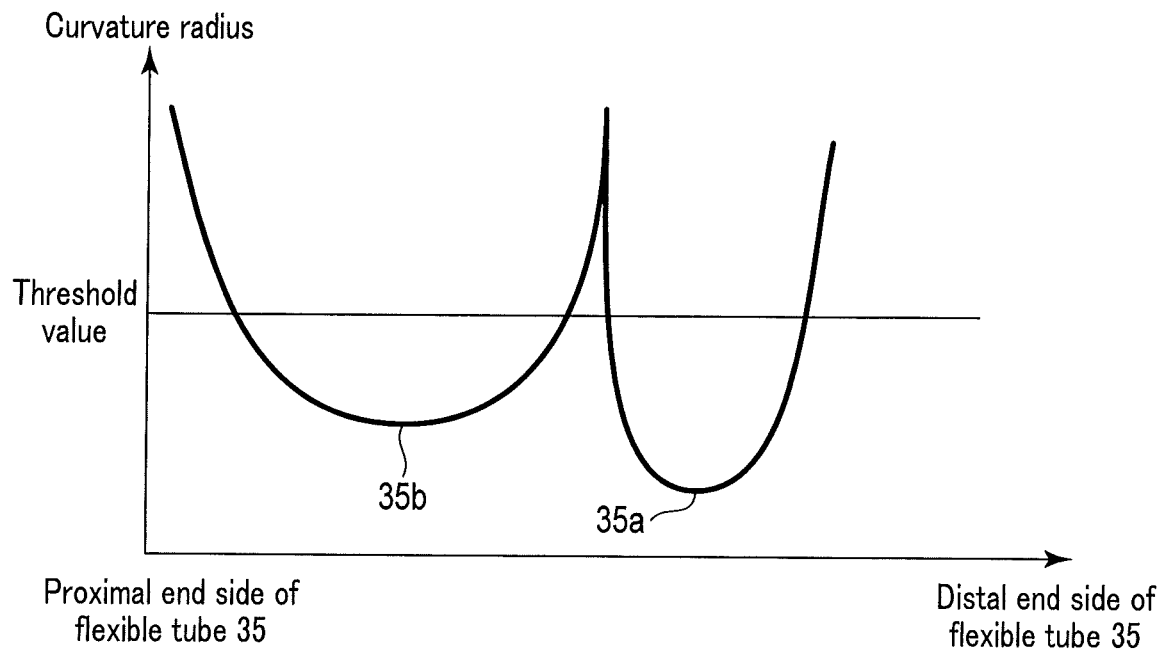
FIG. 2B is a graph for explaining a bent curve line in the bent information.

The bent information includes, for example, bent curve lines shown in FIG. 2B. The bent curve line represents a relationship between each position of the flexible tube 35 and a curvature radius of the flexible tube 35 (each of the bent portions 35a and 35b). The curvature radius is calculated by shape information of the flexible tube 35 obtained by the state detector 50. In this case, the shape information indicates, for example, position information being detection data detected at at least three freely-selected positions.

The bent information calculator 83a outputs the bent information to the determination main section 83b. The bent information calculator 83a starts calculation and always performs calculation after a calculation start instruction is input from the input device 110 in the state in which the calculation results of the state calculator 81 are input. The timing of calculation is not particularly limited, and calculation may be performed for each elapse of a predetermined time.

Figure 2C:
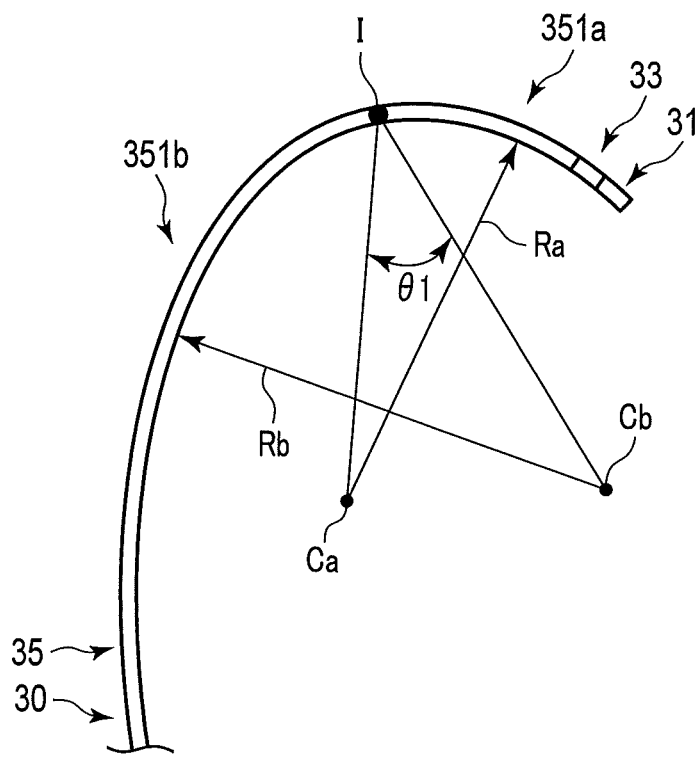
FIG. 2C is a diagram for explaining that a determination main section determines that a shape of the flexible tube is a U shape.

The determination main section 83b determines whether or not both of the bent portion 35a and the bent portion 35b that are bent in directions different from each other are present based on the bent information. For example, the determination main section 83b determines that the shape of the flexible tube 35 is an S shape in a case of an angle θ1>90° as illustrated in FIG. 2A, and determines that the shape of the flexible tube 35 is not an S shape in a case of an angle θ1<90° as illustrated in FIG. 2C. As illustrated in FIG. 2A, the fact that the shape of the flexible tube 35 is an S shape means that both of the bent portion 35a and the bent portion 35b that are bent in directions different from each other are present. As illustrated in FIG. 2C, for example, the fact that the shape of the flexible tube 35 is not an S shape means that even if two bent portions 351a and 351b with bending amounts different from each other are present, the directions of the two bent portions 351a and 351b are the same, and the shape of the flexible tube 35 is a U shape. Alternatively, although not illustrated, for example, the fact that the shape of the flexible tube 35 is not an S shape means that the shape of the flexible tube 35 is a U shape, and only the bent portion is present. As described above, the determination main section 83b determines whether or not the bent portions 35a and 35b are bent in directions different from each other, in other words, determines whether or not the bent portion 35a and the bent portion 35b that is bent in a direction different from that of the bent portion 35a are present in the flexible tube 35.

The determination main section 83b determines whether or not the bent portions 35a and 35b that are bent in directions different from each other each have a predetermined bending amount based on the bending amount included in the bent information and a threshold value set in advance with respect to the bending amount. The threshold value indicates the degree of bending of the bent portions 35a and 35b. The threshold value is, for example, stored in a storage (not shown), and the determination main section 83b reads out the threshold value from the storage as appropriate. The threshold value may input, for example, from the input device 110 to the determination main section 83b. Since the threshold value is different for each patient as appropriate, it may be set for each patient as appropriate.

The determination main section 83b starts determination and always performs determination after a determination start instruction is input from the input device 110 in the state in which the calculation results of the bent information calculator 83a are input. The timing of determination is not particularly limited, and determination may be performed for each elapse of a predetermined time. The determination main section 83b outputs the determination results to the state analysis section 85.

The state analysis section 85 analyzes the respective shape states of the bent portions 35a and 35b based on the bent information calculated by the determining section 83. The state analysis section 85 analyzes the shape state when the determining section 83 determines that the bent portions 35a and 35b that are bent in directions different from each other are formed in the flexible tube 35. Specifically, the state analysis section 85 analyzes the shape state when the determination main section 83b determines that the bent portions 35a and 35b that are bent in directions different from each other each have a predetermined bending amount. The shape state includes, for example, the bent shapes of the entire bent portions 35a and 35b, flat planes 37a and 37b on which the entire bent portions 35a and 35b are arranged, and directions of the flat planes 37a and 37b, as illustrated FIG. 2A and FIG. 3A. The flat plane 37a is a first flat plane, and the flat plane 37b is a second flat plane. The directions of the flat planes 37a and 37b indicate directions of normal lines Na and Nb in the bent portions 35a and 35b. The flat planes 37a and 37b include the center axis of the flexible tube 35 with respect to the insertion direction of the flexible tube 35.

As illustrated in FIG. 2A, in a three-dimensional space including the Xa axis, the Ya axis orthogonal to the Xa axis, and the Za axis orthogonal to the Xa axis and the Ya axis, the flat plane 37a is arranged in the flat plane including the Xa axis and the Ya axis, and the normal line Na extends along the Za axis. Similarly, in a three-dimensional space including the Xb axis, the Yb axis orthogonal to the Xb axis, and the Zb axis orthogonal to the Xb axis and the Yb axis, the flat plane 37b is arranged in the flat plane including the Xb axis and the Yb axis, and the normal line Nb extends along the Zb axis.

Figure 3A:
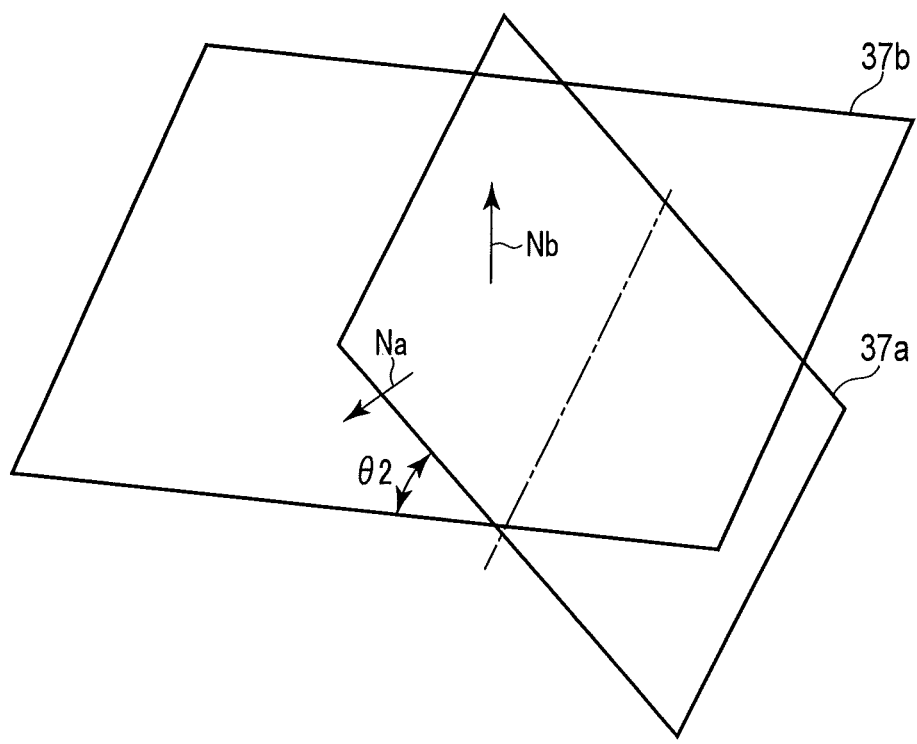
FIG. 3A is a diagram for explaining the shape states.
Figure 4A:
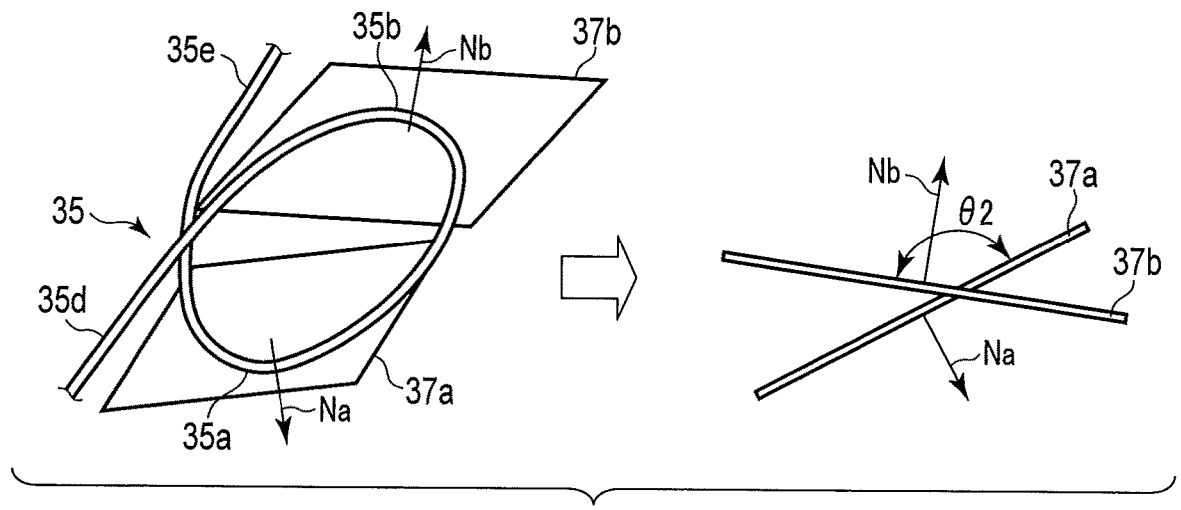
FIG. 4A is a diagram for explaining the angle of the second flat plane with respect to the first flat plane in a state in which a proximal end of an α-shaped portion of the flexible tube is placed on a distal end of the α-shaped portion.
Figure 4B:
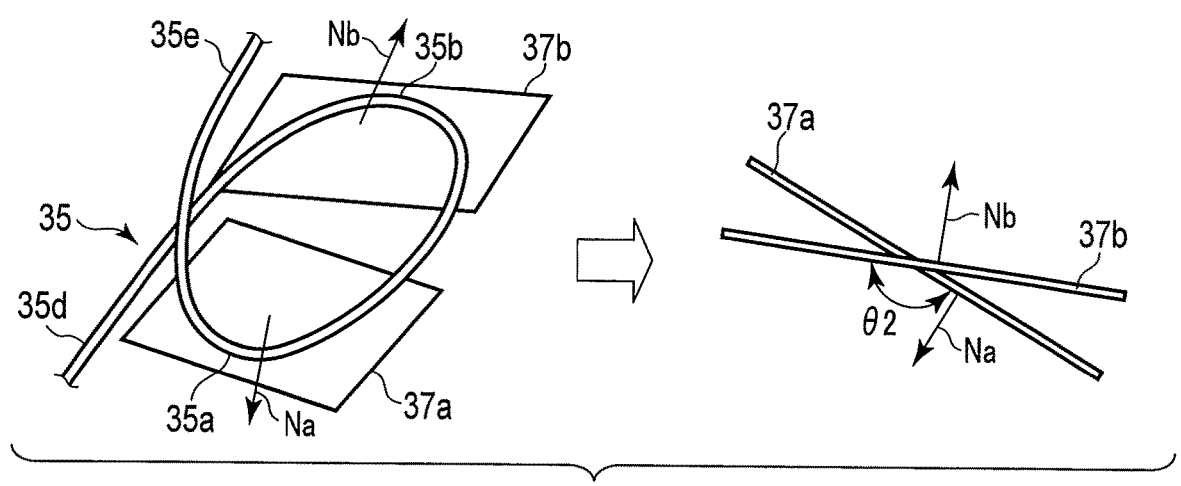
FIG. 4B is a diagram for explaining the angle of the second flat plane with respect to the first flat plane in a state in which the distal end of the α-shaped portion is placed on the proximal end of the α-shaped portion.

As illustrated in FIG. 1, FIG. 2A, and FIG. 3A, the state analysis section 85 includes a flat plane analysis section 85a that is configured to analyze, as a shape state, the flat planes 37a and 37b that include the center axis of the flexible tube 35 with respect to the insertion direction of the flexible tube 35 and on which the entire bent portions 35a and 35b are arranged, and the directions of the flat planes 37a and 37b. Further, the flat plane analysis section 85a analyzes the positional relationship between the flat planes 37a and 37b. For example, the flat plane analysis section 85a analyzes, through analysis of the positional relationship, for example, whether a proximal end 35d of an α-shaped portion of the flexible tube 35 is placed on a distal end 35e of the α-shaped portion (the flat plane 37a is located below the flat plane 37b) as illustrated in FIG. 4A or the distal end 35e of the α-shaped portion is placed on the proximal end 35d of the α-shaped portion (the flat plane 37b is located below the flat plane 37a) as illustrated in FIG. 4B.

The flat plane analysis section 85a starts analysis and always performs analysis after an analysis start instruction is input from the input device 110 in the state in which the determination results of the determination main section 83b are input. The timing of analysis is not particularly limited, and analysis may be performed for each elapse of a predetermined time. The flat plane analysis section 85a outputs the analysis results to the position analysis section 87.

The position analysis section 87 analyzes the relative positional relationship between the bent portions 35a and 35b. The position analysis section 87 analyzes an angular relationship being a positional relationship based on the respective shape states of the bent portions 35a and 35b analyzed by the state analysis section 85, specifically, based on the directions of the flat planes 37a and 37b analyzed by the flat plane analysis section 85a of the state analysis section 85.

Figure 3B:
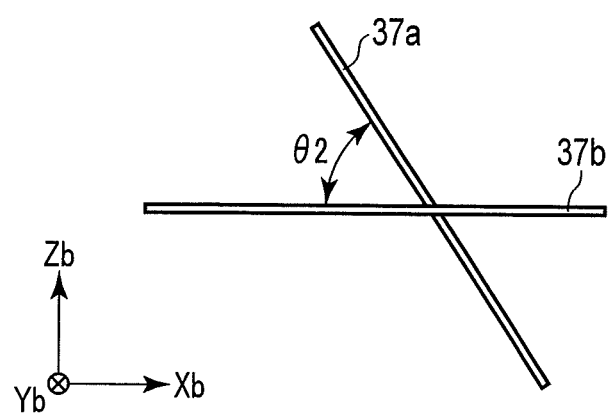
FIG. 3B is a diagram for explaining an angle of a second flat plane with respect to a first flat plane.

As illustrated in FIG. 1, FIG. 3A, and FIG. 3B, the position analysis section 87 includes an angle calculator 87a that is configured to calculate an angle θ2 of the flat plane 37b with respect to the flat plane 37a as an angular relationship being a positional relationship. As illustrated in FIG. 3A and FIG. 3B, the angle calculator 87a calculates, for example, the angle θ2 of the flat plane 37b with respect to the flat plane 37a in the flat plane including the Xb axis and the Zb axis as a relative angle. As illustrated in FIG. 4A and FIG. 4B, for example, when the α-shaped portion is formed, the angle calculator 87a calculates the angular relationship between the flat plane 37a and the flat plane 37b in the flat plane including the Xb axis and the Zb axis. It is assumed that, as illustrated in FIG. 4A, for example, the α-shaped portion is formed, with the proximal end 35d of the α-shaped portion being placed on the distal end 35e of the α-shaped portion. In this case, the angle calculator 87a calculates the angle θ2 formed between the distal end of the flat plane 37a and the proximal end of the flat plane 37b. It is assumed that, as illustrated in FIG. 4B, for example, the α-shaped portion is formed, with the distal end 35e of the α-shaped portion being placed on the proximal end 35d of the α-shaped portion. In this case, the angle calculator 87a calculates the angle θ2 formed between the distal end of the flat plane 37a and the proximal end of the flat plane 37b.

The angle calculator 87a starts calculation and always performs calculation after a calculation start instruction is input from the input device 110 in the state in which the analysis results of the flat plane analysis section 85a are input. The timing of calculation is not particularly limited, and calculation may be performed for each elapse of a predetermined time. The angle calculator 87a outputs the calculation results to the rotation calculator 89.

Figure 3C:
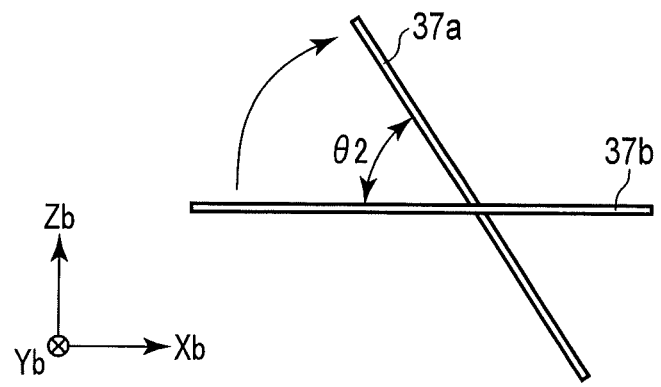
FIG. 3C is a diagram for explaining a rotation direction and a rotation amount of the second flat plane with respect to the first flat plane.

As illustrated in FIG. 3C, the rotation calculator 89 calculates a rotation direction and a rotation amount of the shape state of the bent portion 35b for rotating the shape state of the bent portion 35b toward the shape state of the bent portion 35a so that the shape states of the bent portions 35a and 35b become substantially identical with each other based on the angular relationship being the positional relationship. The rotation calculator 89 calculates a rotation direction and a rotation amount of the flat plane 37b with respect to the flat plane 37a so that the flat plane 37a is arranged on the substantially identical flat plane with the flat plane 37b, in other words, the angle θ2 calculated by the angle calculator 87a approximates substantially 0°. As long as the flat plane 37b is arranged on the substantially identical flat plane with the flat plane 37a, at least a part of the flat plane 37b may overlap with the flat plane 37a. Therefore, the flat plane 37b may be arranged while being displaced from the flat plane 37a. The rotation calculator 89 starts calculation and always performs calculation after a calculation start instruction is input from the input device 110 in the state in which the calculation results of the angle calculator 87a are input. The timing of calculation is not particularly limited, and calculation may be performed for each elapse of a predetermined time. The rotation calculator 89 outputs the calculation results to the shape changing section 91.

Figure 3D:
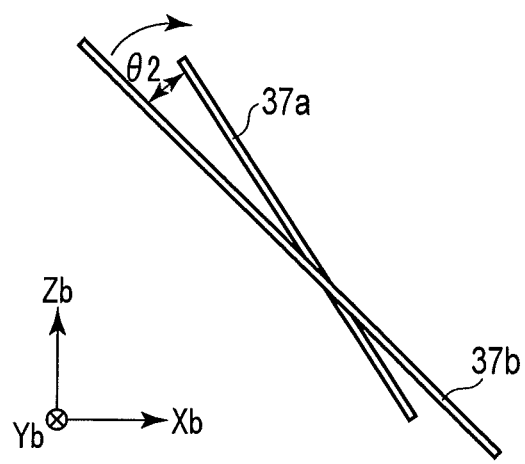
FIG. 3D is a diagram for explaining rotation of the second flat plane with respect to the first flat plane.

As illustrated in FIG. 1, FIG. 3D, and FIG. 5A, the shape changing section 91 actively changes the shape state of the bent portion 35*b* in accordance with the rotation direction and the rotation amount calculated by the rotation calculator 89. The shape changing section 91 is arranged in the flexible tube 35. For example, the shape changing section 91 actively rotates the entire bent portion 35*b* in accordance with the rotation direction and the rotation amount calculated by the rotation calculator 89 so that the angle θ2 is changed to substantially 0° and the flat plane 37*b* is arranged on the substantially identical flat plane with the flat plane 37*a*. That is, the shape changing section 91 actively rotates (controls) the flexible tube 35, in other words, performs rotation operation of the flexible tube 35, in place of an operator. Further, in other words, the shape changing section 91 applies a rotation force in the rotation operation by the shape changing section 91 to the flexible tube 35 in place of a rotation force in rotation operation by an operator.

As illustrated in FIG. 5A, the shape changing section 91 includes an elongated linear member 91*a* having a desired length, and a driver 91*b* that is configured to drive the linear member 91*a* by a drive force in accordance with the rotation direction and the rotation amount. The linear member 91*a* is separate from the bendable section 33 and the flexible tube 35. The linear member 91*a* may further be arranged in the bendable section 33. The linear member 91*a* may be embedded in the flexible tube 35. The linear member 91*a* may be, for example, positioned assuming a position at which the bent portion 35*b* is to be formed. The linear member 91*a* is, for example, a metal wire. The distal end of the linear member 91*a* is coupled to the driver 91*b*, and the proximal end of the linear member 91*a* is fixed to the inside of the flexible tube 35. For example, drive of the linear member 91*a* indicates rotation, pulling, or pressing by the driver 91*b*. The driver 91*b* includes a motor that is configured to generate a drive force for driving the linear member 91*a*. The driver 91*b* is arranged at the distal end of the linear member 91*a* arranged on the bendable section 33 side. As illustrated in FIG. 5B, another driver 91*b* may further be arranged at the proximal end of the linear member 91*a* arranged on the control section 40 side. A driver 91*b* may be arranged only at the proximal end of the linear member 91*a*. The driver 91*b* is electrically connected to the rotation calculator 89, and transmits a drive force in accordance with the rotation direction and the rotation amount calculated by the rotation calculator 89 to the linear member 91*a*. The linear member 91*a* drives by a drive force so that the angle θ2 is changed to substantially 0°, and by the drive, rotates the bent portion 35*b* toward the bent portion 35*a*. The matter that the angle θ2 is changed to substantially 0° means that the flat plane 37*b* is arranged on the substantially identical flat plane with the flat plane 37*a*.

It may be configured that the linear member 91*a* is omitted, and the drive force of the driver 91*b* is directly transmitted to the flexible tube 35. The configuration of the shape changing section 91 is not particularly limited as long as rotation operation of the flexible tube 35 can be performed, and, for example, a shape memory alloy may be used.

The shape changing section 91 starts operation when the calculation results calculated by the rotation calculator 89 are input. For example, when the rotation calculator 89 calculates that the angle θ2 is changed to substantially 0°, the shape changing section 91 ends the operation. The operation start and operation end of the shape changing section 91 are not limited thereto. For example, the display 130 displays the shape information calculated by the state calculator 81. An operator may control drive of the shape changing section 91 in consideration of the shape information displayed on the display 130.

In view of this, as a first example of the operation start and operation end by an operator, as illustrated in FIG. 1, when the input device 110 inputs an operation start instruction of the shape changing section 91 from the input device 110 to the shape changing section 91, the shape changing section 91 may start change. When the input device 110 inputs a change end instruction of the shape changing section 91 from the input device 110 to the shape changing section 91, the shape changing section 91 may end the change. The input device 110 in this case is operated by an operator, and may be, for example, a button switch arranged in the control section 40 or a foot switch electrically connected to the endoscope 20.

As a second example of the operation start and operation end by an operator, as illustrated in FIG. 6, the insertion apparatus 10 may include a gripping rotation calculator 95*a*, a rotation detector 95*b*, and an instruction section 95*c*. The gripping rotation calculator 95*a*, the rotation detector 95*b*, and the instruction section 95*c* are arranged in the controller 80. The gripping rotation calculator 95*a*, the rotation detector 95*b*, and the instruction section 95*c* are configured by, for example, a hardware circuit including an ASIC or the like. At least one of the gripping rotation calculator 95*a*, the rotation detector 95*b*, and the instruction section 95*c* may be configured by a processor. When at least one of those is configured by a processor, an internal memory or an external memory (not shown) to which the processor is accessible is arranged. The internal memory or the external memory stores a program code for causing the processor to function as at least one of those when the processor performs execution.

The gripping rotation calculator 95*a* calculates, based on state information detected by the state detector 50, a rotation direction of a gripped portion 38 of the flexible tube 35 (see FIG. 2A) that is gripped by an operator. In this case, for example, the state detector 50 may include any of an energy sensor, a torque sensor, a strain sensor, an acceleration sensor, and a position sensor. The gripped portion 38 is arranged on the center axis of the flexible tube 35. The rotation direction indicates a direction about the center axis of the flexible tube 35. The gripping rotation calculator 95*a* outputs the calculation results to the rotation detector 95*b*.

The rotation detector 95*b* detects whether or not the gripping rotation calculator 95*a* performs calculation, that is, detects rotation of the gripped portion 38 by an operator. The rotation detector 95*b* outputs the detection results to the instruction section 95*c*.

When the rotation detector 95*b* detects that the gripping rotation calculator 95*a* performs calculation, the instruction section 95*c* instructs (outputs) an operation start instruction of the shape changing section 91 to the shape changing section 91. When the rotation detector 95*b* detects that the gripping rotation calculator 95*a* does not perform calculation, the instruction section 95*c* instructs (outputs) the operation end instruction of the shape changing section 91 to the shape changing section 91.

Hereinafter, an example of drive of the insertion apparatus 10 will be briefly described.

When the flexible tube 35 proceeds toward a deep portion of a large intestine along an intestine wall of the large intestine, the distal end of the flexible tube 35 passes through the sigmoid colon to reach an SD bent portion. The bent portion 35a is formed on the flexible tube 35 in the SD bent portion, and the bent portion 35b is formed in the sigmoid colon. At this time, the flexible tube 35 inside the large intestine may be arranged three-dimensionally while winding in various directions rather than being arranged two-dimensionally on a substantially identical flat plane. Therefore, as illustrated in FIG. 7A, the flat plane 37a on which the bent portion 35a may be arranged substantially orthogonal to the flat plane 37b without being arranged on the substantially identical flat plane with the flat plane 37b on which the bent portion 35b is arranged.

Figure 7A:
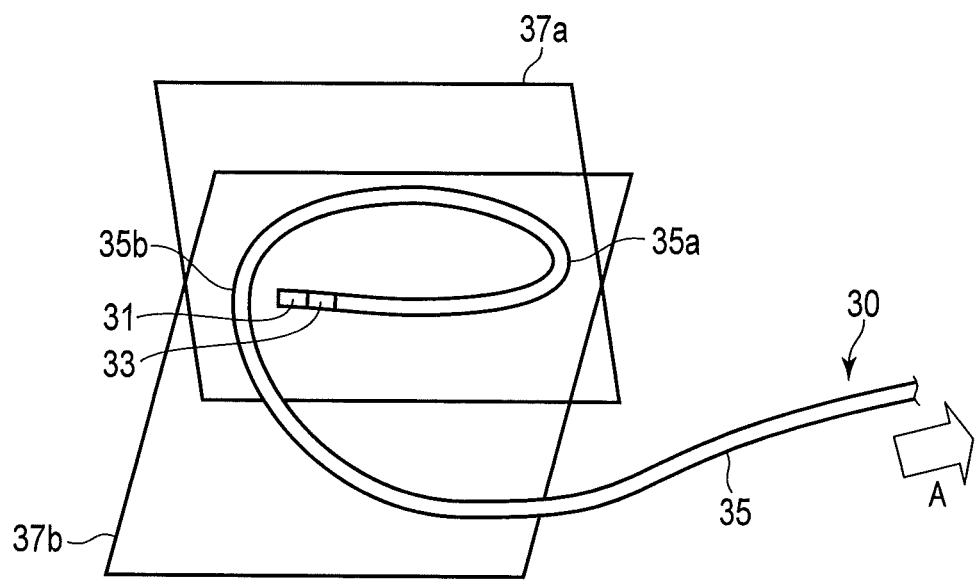
FIG. 7A is a diagram for explaining drawing operation in a state in which the first flat plane is arranged so as to be substantially orthogonal to the second flat plane.
Figure 7B:
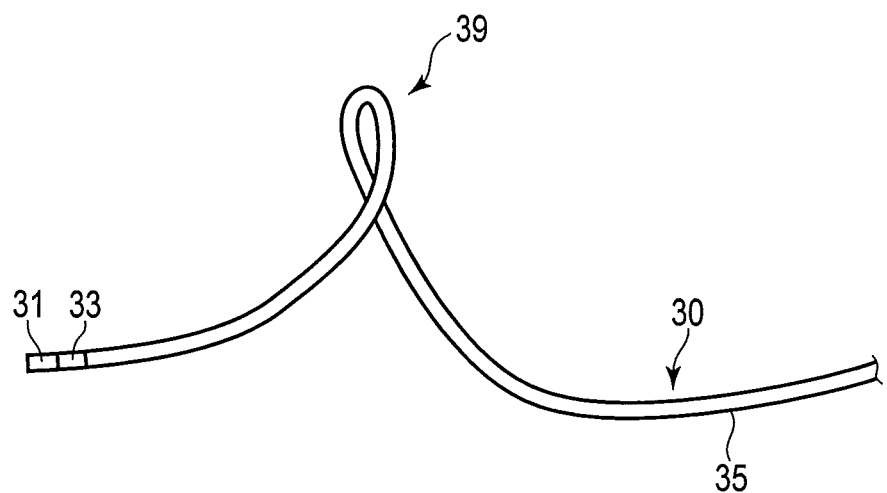
FIG. 7B is a diagram for explaining that a loop portion may be formed by the drawing operation illustrated in FIG. 7A.

In the state, it is assumed that rotation (twisting) operation in a substantially straightened procedure is not performed on the flexible tube 35 or is not sufficiently performed, and drawing operation in the substantially straightened procedure indicated by the arrow A in FIG. 7A is performed on the flexible tube 35. Then, as illustrated in FIG. 7B, the flexible tube 35 may be entangled, in other words, the entire flexible tube 35 may be twisted, further in other words, a loop portion 39 may be formed on the flexible tube 35. Further, the distal end of the flexible tube 35 may fall out from the SD bent portion to a hand (gripped portion 38) side. In such a state, even when formation of the loop portion 39 is tried to be eliminated so that the flexible tube 35 is changed to substantially a straight shape, the flexible tube 35 cannot be changed to substantially the straight shape. Therefore, even when the flexible tube 35 is pushed from the hand side in the state, the pushing force on the hand side is not easily transmitted to the distal end, so that the proceeding of the flexible tube 35 to the deep portion is not easy. Therefore, it is necessary to perform rotation operation of arranging the flat plane 37b on the substantially identical flat plane with the flat plane 37a and eliminating formation of the loop portion 39 by drawing operation in the arrangement state. Specifically, when the flat plane 37a is arranged on the substantially identical flat plane with the flat plane 37b, even though the drawing operation is performed on the flexible tube 35, entanglement in the flexible tube 35 is suppressed, in other words, twisting of the entire flexible tube 35 is suppressed, further in other words, formation of the loop portion 39 in the flexible tube 35 is eliminated. That is, in the flexible tube 35 including the bent portions 35a and 35b, it is preferable that the flat plane 37a is arranged on the substantially identical flat plane with the flat plane 37b.

In view of this, when the rotation operation is performed by an operator, it is necessary for an operator to apply a large force enough to lift up the entire bent portion 35b to the flexible tube 35 as a rotation force on the hand side in the rotation operation, so that the burden of the operator becomes larger.

In view of this, in this embodiment, the state calculator 81 calculates shape information of the flexible tube 35 inserted into the body. The determining section 83 calculates bent information based on the shape information to determine whether or not the flexible tube 35 including the bent portions 35a and 35b that are bent in directions different from each other is formed based on the bent information. When the flexible tube 35 including the bent portions 35a and 35b is formed, the state analysis section 85 analyzes the respective shape states of the bent portions 35a and 35b based on the bent information. The shape state includes the bent shape of each of the entire bent portions 35a and 35b, the flat planes 37a and 37b on which the entire bent portions 35a and 35b are arranged, and the directions of the flat planes 37a and 37b. The position analysis section 87 calculates the angle θ2 of the flat plane 37b with respect to the flat plane 37a as an angular relationship based on the directions of the flat planes 37a and 37b of the shape state. The rotation calculator 89 calculates a rotation direction and a rotation amount of the flat plane 37b with respect to the flat plane 37a based on the angular relationship so that the angle θ2 becomes substantially 0°, in other words, the flat plane 37b is arranged on the substantially identical flat plane with the flat plane 37a. For example, the shape changing section 91 starts operation by manual operation through the input device 110. As indicated by the arrow in FIG. 8A, the shape changing section 91 actively changes the shape state of the bent portion 35b in accordance with the rotation direction and the rotation amount. With this, as illustrated in FIG. 8B, the flat plane 37b is arranged on the substantially identical flat plane with the flat plane 37a by a drive force of the shape changing section 91. For example, the shape changing section 91 ends the operation by manual operation through the input device 110.

As illustrated in FIG. 8B, the flat plane 37b is arranged on the substantially identical flat plane with the flat plane 37a by the rotation operation by the shape changing section 91, and hence a rotation force in rotation operation by an operator that is necessary for eliminating the loop portion is reduced, so that the burden of an operator is reduced. In other words, the shape changing section 91 performs the rotation operation, and the shape changing section 91 actively rotates (controls) the flexible tube 35. Therefore, the burden of an operator is reduced. The rotation operation may become unnecessary in some cases.

Figure 8C:
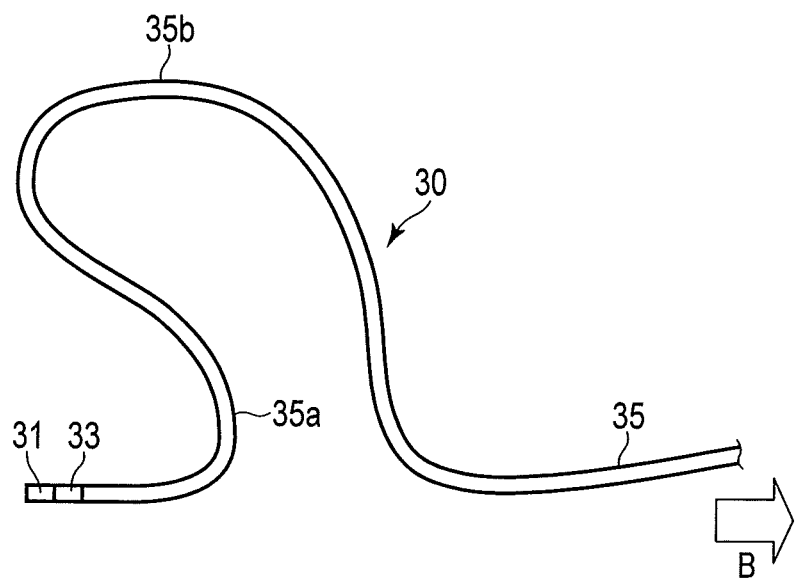
FIG. 8C is a diagram for explaining the drawing operation with respect to the state illustrated in FIG. 8B.
Figure 8D:
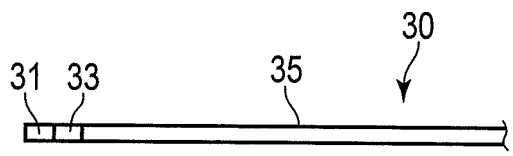
FIG. 8D is a diagram for explaining that the flexible tube is changed to substantially the straight shape by the drawing operation illustrated in FIG. 8C.

The flat plane 37a is arranged on the substantially identical flat plane with the flat plane 37b. Thus, even when the drawing operation indicated by the arrow B in FIG. 8C is performed on the flexible tube 35, entanglement in the flexible tube 35 is suppressed, in other words, twisting of the entire flexible tube 35 is suppressed, further in other words, formation of the loop portion 39 in the flexible tube 35 is eliminated. Therefore, when the drawing operation is performed on the flexible tube 35, the bent portions 35a and 35b are eliminated, and as illustrated in FIG. 8D, the flexible tube 35 inside the large intestine is easily changed to substantially the straight shape. Along with this change, the intestine tract from an inlet of the intestine tract to the SD bent portion at which the distal end of the flexible tube 35 is arranged is changed to substantially the straight shape. Then, the pushing force on the hand side is easily transmitted to the distal end, so that the distal end can easily proceed toward the deep portion by pushing. That is, when the pushing operation is performed, the flexible tube 35 in substantially the straight shape easily proceeds toward the deep portion.

In this embodiment, since the flat plane 37b can be arranged on the substantially identical flat plane with the flat plane 37a by the shape changing section 91, it becomes unnecessary for an operator to apply a large force as a rotation force to the flexible tube 35 in the rotation operation, so that the burden of an operator can be reduced. Further, even when the rotation operation is necessary, a force applied to the flexible tube 35 as a rotation force can be small, so that the burden of an operator can be reduced. In this embodiment, since the flat plane 37b can be arranged on the substantially identical flat plane with the flat plane 37a by the shape changing section 91, even when the drawing operation is performed, formation of the loop portion 39 in the flexible tube 35 can be eliminated. As described above, in this embodiment, formation of the loop portion 39 in the flexible tube 35 can be eliminated in the state in which the burden of an operator can be reduced.

In this embodiment, in place of providing a rotation (twisting) direction for eliminating the already formed loop portion 39 as information, the flat plane 37b is arranged on the substantially identical flat plane with the flat plane 37a by the shape changing section 91. Therefore, in this embodiment, the rotation operation performed by an operator can be unnecessary, so that the burden of an operator can be directly reduced.

In this embodiment, the flat plane 37b is arranged on the substantially identical flat plane with the flat plane 37a by the shape changing section 91, in other words, the rotation operation is performed by the shape changing section 91, and then the shape changing section 91 actively rotates (controls) the flexible tube 35. Therefore, the burden of an operator can be reduced.

In this embodiment, the bent portions 35a and 35b formed on the flexible tube 35 can be easily eliminated by the drawing operation, and the flexible tube 35 can be easily changed to substantially the straight shape. Therefore, the pushing force on the hand side can be easily transmitted to the distal end, and the distal end can easily proceed toward the deep portion by pushing. That is, by pushing operation, the flexible tube 35 in substantially the straight shape can easily proceed toward the deep portion, and the insertion of the flexible tube 35 can be improved, so that the proceeding of the flexible tube 35 can be directly assisted.

In this embodiment, the determination main section 83b determines presence of the bent portions 35a and 35b that are bent in directions different from each other. Therefore, the bent portions 35a and 35b can be accurately determined. In this embodiment, the determination main section 83b determines a portion in which a curvature radius is lower than a threshold value as the bent portions 35a and 35b. Therefore, the burden of the shape changing section 91 that is configured to actively change the bent portion 35b can be reduced.

In this embodiment, the flat plane analysis section 85a analyzes the flat planes 37a and 37b and the directions of the flat planes 37a and 37b. Therefore, in this embodiment, the state of each of the bent portions 35a and 35b can be easily analyzed.

In this embodiment, the angle calculator 87a calculates the angle of the flat plane 37b with respect to the flat plane 37a as the angular relationship. Therefore, in this embodiment, the relative angular relationship between the flat planes 37a and 37b can be easily calculated.

In this embodiment, the rotation calculator 89 calculates the rotation direction and the rotation amount of the flat plane 37b with respect to the flat plane 37a such that the flat plane 37a is arranged on the substantially identical flat plane with the flat plane 37b. Therefore, in this embodiment, the flat plane 37b can be arranged on the substantially identical flat plane with the flat plane 37a.

In this embodiment, the input device 110 inputs the operation start instruction of the shape changing section 91 to the shape changing section 91. Therefore, in this embodiment, an operator can control drive of the shape changing section 91 by operation by the input device 110 in consideration of the shape information displayed on the display 130.

In this embodiment, an operator performs the rotation operation in consideration of the shape information displayed on the display 130. The rotation direction in this operation is calculated by the gripping rotation calculator 95a, and the rotation operation is detected by the rotation detector 95b. Then, the instruction section 95c outputs the operation start instruction to the shape changing section 91. Therefore, operation start of the shape changing section 91 can be controlled in conjunction with the rotation operation by the operator.

Note that, the invention of the present application is not limited to the embodiments described above, and can be variously modified within the range of not departing from the gist of the present invention in an implementation phase. Further, the embodiments described above may be carried out in combination as appropriate to the extent possible, and in this case, combined effects are obtained. Moreover, the embodiments described above include inventions in various stages, and various inventions may be extracted by an appropriate combination selected from plurality of components disclosed. For example, if the problems can be solved and the effects can be obtained even when some components are delated from all the components described in the embodiments, configurations obtained by deleting the components may be extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
a processor comprising hardware, the processor being configured to:
receive state information indicating information of a flexible tube configured to be inserted into an insertion target body, the state information relating to a shape of the flexible tube;
determine, based on the received state information, whether a first bent portion on a distal end side of the flexible tube and a second bent portion on a proximal end side of the flexible tube are formed in a configuration on the flexible tube based on the state where the first bent portion and the second bent portion are bent in directions different from each other with an inflection point interposed between the first bent portion and the second bent portion; and
when the processor determines that the first bent portion and the second bent portion are formed in the configuration, control a shape changing actuator configured to actively change the shape of the flexible tube to reduce an angle at which a first virtual flat plane on which the first bent portion is formed and a second virtual flat plane on which the second bent portion is formed intersect with each other.

2. A flexible tube insertion apparatus comprising:
a processor comprising hardware, the processor being configured to:
receive state information indicating information of a flexible tube configured to be inserted into an insertion target body, the state information relating to a shape of the flexible tube;
determine, based on the received state information, whether a first bent portion on a distal end side of the flexible tube and a second bent portion on a proximal end side of the flexible tube are formed in a configuration where the first bent portion and the second bent portion are bent in directions different from each other;

when the processor determines that the first bent portion and the second bent portion are formed in the configuration, control a shape changing actuator configured to actively change the shape of the flexible tube to reduce an angle at which a first virtual flat plane on which the first bent portion is formed and a second virtual flat plane on which the second bent portion is formed intersect with each other;

when the processor determines that the first bent portion and the second bent portion are formed in the configuration, analyze shape states of the first bent portion and the second bent portion based on the state information;

analyze a relative positional relationship between the first bent portion and the second bent portion based on the respective analyzed shape states of the first bent portion and the second bent portion;

based on the positional relationship, calculate a rotation direction and a rotation amount of the shape state of the second bent portion for rotating the shape state of the second bent portion toward the shape state of the first bent portion so that the angle at which the first virtual flat plane and the second virtual flat plane intersect with each other becomes smaller.

3. The flexible tube insertion apparatus according to claim 2, wherein the processor is configured to:
calculate bent information of the flexible tube based on the state information; and
determine whether or not the first bent portion and the second bent portion are bent in the configuration based on the bent information.

4. The flexible tube insertion apparatus according to claim 3, wherein the processor is configured to calculate, as the shape states, directions of flat planes that include a center axis of the flexible tube with respect to an insertion direction and on which the first bent portion and the second bent portion are arranged.

5. The flexible tube insertion apparatus according to claim 4, wherein the processor is configured to calculate an angle of the second virtual flat plane on which the entire second bent portion is arranged with respect to the first virtual flat plane on which the entire first bent portion is arranged as an angular relationship being the positional relationship.

6. The flexible tube insertion apparatus according to claim 5, wherein the processor calculates the rotation direction and the rotation amount of the second virtual flat plane with respect to the first virtual flat plane so that the angle at which the first virtual flat plane and the second virtual flat plane intersect with each other becomes smaller.

7. The flexible tube insertion apparatus according to claim 6, further comprising the shape changing actuator, wherein the shape changing actuator comprises:
an elongated linear member that has a desired length and is separate from a bendable section and the flexible tube; and
a driver that is arranged at a distal end of the linear member arranged on a side of the bendable section and is configured to drive the linear member by a drive force in accordance with the rotation direction and the rotation amount,
wherein the linear member rotates the second bent portion toward the first bent portion by the drive force so that the angle approaches 0°.

8. The flexible tube insertion apparatus according to claim 7, wherein the driver is further arranged at a proximal end of the linear member.

9. The flexible tube insertion apparatus according to claim 2, further comprising an input device that is configured to input an operation start instruction of the shape changing actuator to the shape changing actuator.

10. The flexible tube insertion apparatus according to claim 2, wherein the processor is further configured to:
calculate a rotation direction of a gripped portion of the flexible tube that is gripped based on the state information;
detect whether or not the rotation direction of the gripped portion of the flexible tube is calculated; and
instruct an operation start instruction of the shape changing actuator to the shape changing actuator when the the rotation direction of the gripped portion of the flexible tube is calculated.

11. A flexible tube insertion method comprising:
receiving state information of a flexible tube inserted into an insertion target body, the state information relating to a shape of the flexible tube;
determining, based on the received state information, whether a first bent portion on a distal end side of the flexible tube and a second bent portion on a proximal end side of the flexible tube are formed in a configuration where the first bent portion and the second bent portion are bent in directions different from each other with an inflection point interposed between the first bent portion and the second bent portion; and
when the first bent portion and the second bent portion are determined to be formed in the configuration, control a shape changing actuator configured to actively change the shape of the flexible tube to reduce an angle at which a first virtual flat plane on which the first bent portion is formed and a second virtual flat plane on which the second bent portion is formed intersect with each other.

12. A flexible tube insertion method comprising:
receiving state information of a flexible tube inserted into an insertion target body, the state information relating to a shape of the flexible tube;
determining, based on the received state information, whether a first bent portion on a distal end side of the flexible tube and a second bent portion on a proximal end side of the flexible tube are formed in a configuration where the first bent portion and the second bent portion are bent in directions different from each other;
when the first bent portion and the second bent portion are determined to be formed in the configuration, controlling a shape changing actuator configured to actively change the shape of the flexible tube to reduce an angle at which a first virtual flat plane on which the first bent portion is formed and a second virtual flat plane on which the second bent portion is formed intersect with each other;
when the first bent portion and the second bent portion are determined to be formed in the configuration, analyzing shape states of the first bent portion and the second bent portion based on the state information;
analyzing a relative positional relationship between the first bent portion and the second bent portion based on the respective analyzed shape states of the first bent portion and the second bent portion;
based on the positional relationship, calculating a rotation direction and a rotation amount of the shape state of the second bent portion for rotating the shape state of the second bent portion toward the shape state of the first bent portion so that the angle at which the first virtual flat plane and the second virtual flat plane intersect with each other becomes smaller.

13. The flexible tube insertion method according to claim 12, wherein the determining whether or not the first bent portion and the second bent portion are formed in the configuration includes calculating bent information of the flexible tube, and determining whether or not the first bent portion and the second bent portion that are bent in the configuration based on the bent information.

14. The flexible tube insertion method according to claim 13, wherein the analyzing the shape states includes calculating, as the shape states, directions of flat planes that include a center axis of the flexible tube with respect to an insertion direction and on which the first bent portion and the second bent portion are arranged.

15. The flexible tube insertion method according to claim 14, wherein the analyzing the positional relationship includes calculating an angle of the second virtual flat plane on which the entire second bent portion is arranged with respect to the first virtual flat plane on which the entire first bent portion is arranged as an angular relationship being the positional relationship.

16. The flexible tube insertion method according to claim 15, wherein the calculating the rotation amount includes calculating a rotation direction and a rotation amount of the second virtual flat plane with respect to the first virtual flat plane so that the angle at which the first virtual flat plane and the second virtual flat plane intersect with each other becomes smaller.

17. The flexible tube insertion method according to claim 16, wherein the shape changing actuator includes:
an elongated linear member that has a desired length and is separate from a bendable section and the flexible tube; and
a driver that is arranged at a distal end of the linear member arranged on a side of the bendable section and is configured to drive the linear member by a drive force in accordance with the rotation direction and the rotation amount,
wherein the linear member rotates the second bent portion toward the first bent portion by the drive force so that the angle approaches 0°.

18. The flexible tube insertion method according to claim 17, wherein the driver is further arranged at a proximal end of the linear member.

19. The flexible tube insertion method according to claim 12, further comprising an input device that is configured to input an operation start instruction of the shape changing actuator to the shape changing actuator.

20. The flexible tube insertion method according to claim 12, further comprising;
calculating a rotation direction of a gripped portion of the flexible tube that is gripped based on the state information;
detecting whether or not the rotation direction of the gripped portion of the flexible tube is calculated; and
instructing an operation start of the shape changing actuator to the shape changing actuator when it is detected that the rotation direction of the gripped portion of the flexible tube is calculated.

* * * * *